(12) United States Patent
Radmand et al.

(10) Patent No.: US 11,813,441 B2
(45) Date of Patent: Nov. 14, 2023

(54) REUSABLE NEEDLE HANDLING APPARATUS

(71) Applicant: Achaemenid, LLC, Stratford, CT (US)

(72) Inventors: Reza Radmand, Boston, MA (US); Stephen J Cole, White Plains, NY (US)

(73) Assignee: ACHAEMENID, LLC, Stratford, CT (US)

( * ) Notice: Subject to any disclaimer, the term of this patent is extended or adjusted under 35 U.S.C. 154(b) by 886 days.

(21) Appl. No.: 16/652,750

(22) PCT Filed: Oct. 10, 2018

(86) PCT No.: PCT/US2018/055114
§ 371 (c)(1),
(2) Date: Apr. 1, 2020

(87) PCT Pub. No.: WO2019/089197
PCT Pub. Date: May 9, 2019

(65) Prior Publication Data
US 2020/0230327 A1    Jul. 23, 2020

Related U.S. Application Data

(60) Provisional application No. 62/578,692, filed on Oct. 30, 2017.

(51) Int. Cl.
*A61M 5/32* (2006.01)
*A61M 5/34* (2006.01)

(52) U.S. Cl.
CPC .......... *A61M 5/3276* (2013.01); *A61M 5/347* (2013.01); *A61M 2005/3208* (2013.01)

(58) Field of Classification Search
CPC ........ A61M 2005/3208; A61M 5/3205; A61M 5/321; A61M 5/3213; A61M 5/3276; A61M 5/347; A61M 5/3202; A61M 5/3204; A61B 50/3001; A61B 50/362
See application file for complete search history.

(56) References Cited

U.S. PATENT DOCUMENTS

| 3,921,841 A | 11/1975 | Mizutani et al. |
| 4,798,587 A * | 1/1989 | Willoughby ........ A61M 5/3205 604/110 |
| 4,867,309 A | 9/1989 | Germain |

(Continued)

OTHER PUBLICATIONS

International Searching Authority, International Preliminary Report on Patentability for PCT App. No. PCT/US2018/055114, dated May 5, 2020, 6 pgs.

(Continued)

*Primary Examiner* — Shefali D Patel
(74) *Attorney, Agent, or Firm* — WOMBLE BOND DICKINSON (US) LLP (57) ABSTRACT

A reusable needle handling apparatus is described. The needle handling apparatus is configured for receiving at least a portion of a syringe assembly including at least a needle, a needle cap, and a syringe hub. The needle handling apparatus includes a first clamping mechanism having a plurality of pinch rollers. According to an aspect, the pinch rollers are configured to clamp the needle cap, and to automatically unscrew the needle from the syringe hub, so that the needle is safely and automatically removed from the syringe hub.

10 Claims, 6 Drawing Sheets

(56) References Cited

U.S. PATENT DOCUMENTS

| | | | |
|---|---|---|---|
| 4,986,811 A | 1/1991 | Thead et al. | |
| 5,482,207 A | 1/1996 | Nelson et al. | |
| 5,761,975 A | 6/1998 | Waluda | |
| 6,202,843 B1 | 3/2001 | Kelson et al. | |
| 10,258,746 B2 | 4/2019 | Radmand et al. | |
| 2005/0236289 A1* | 10/2005 | Tanaka ................ | A61M 5/3205 206/370 |
| 2013/0150804 A1 | 6/2013 | Bianco et al. | |
| 2015/0297838 A1 | 10/2015 | Steel et al. | |
| 2017/0173272 A1 | 6/2017 | Radmand et al. | |

OTHER PUBLICATIONS

International Searching Authority, International Search Report and Written Opinion of International App. No. PCT/US2018/055114, dated Jan. 3, 2019, 14 pgs.

* cited by examiner

REUSABLE NEEDLE HANDLING APPARATUS

CROSS-REFERENCE TO RELATED APPLICATIONS

This application is a national phase application of and claims priority to Patent Cooperation Treaty (PCT) Application No. PCT/US2018/055114 filed Oct. 10, 2018, which claims the benefit of U.S. Provisional Application No. 62/578,692 filed Oct. 30, 2017, each of which is incorporated herein by reference in its entirety.

FIELD OF THE DISCLOSURE

An apparatus and method of automatically and safely removing a needle from a syringe assembly while retaining a hub as part of the syringe assembly is generally described.

BACKGROUND OF THE DISCLOSURE

As is commonly known by those of ordinary skill in the art, maintaining safety of healthcare personnel who handle needles in a healthcare setting is an ongoing problem.

Figure 1:
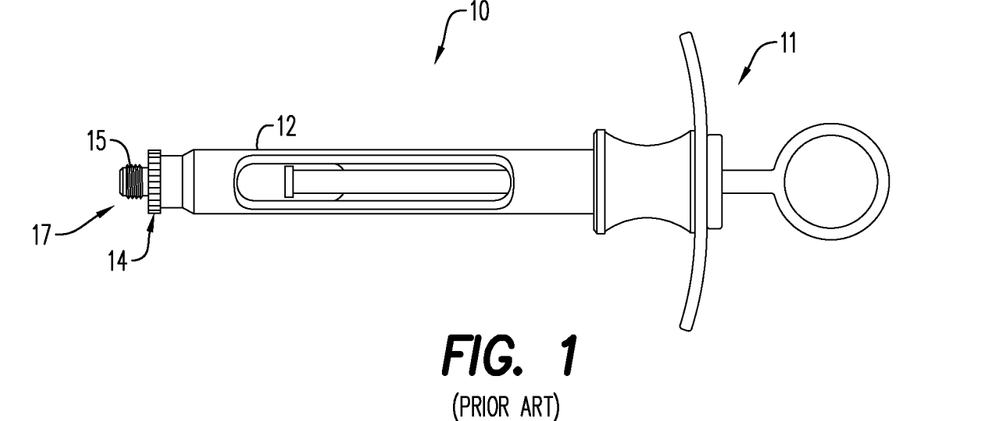
FIG. 1 is a side perspective view of a prior art syringe assembly.
Figure 2:
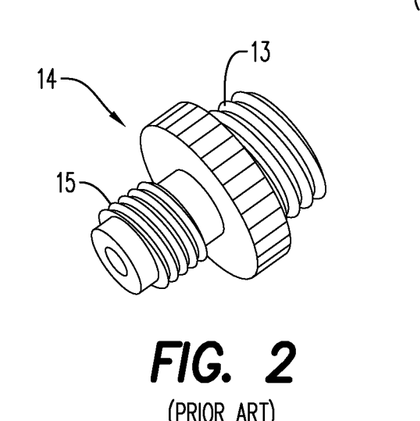
FIG. 2 is a perspective view of a needle end of the syringe assembly of FIG. 1.
Figure 3:
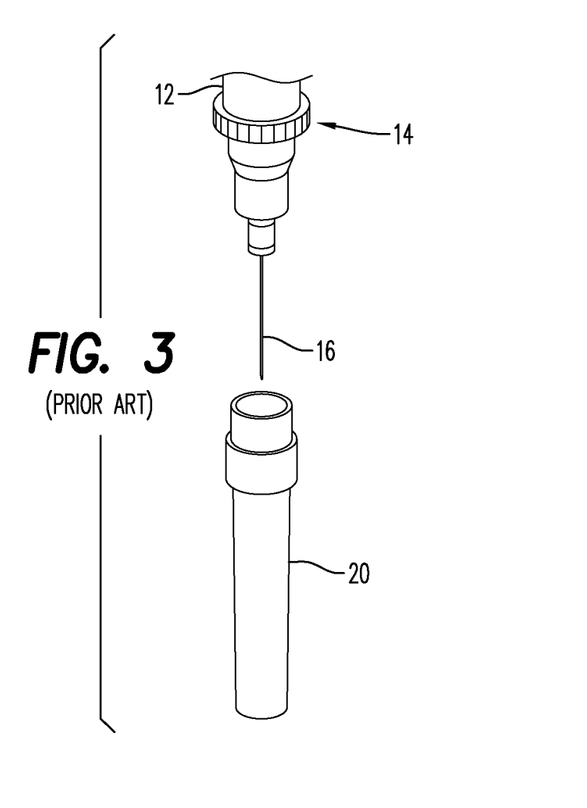
FIG. 3 is an exploded perspective view of a syringe hub useful as part of the syringe assembly of FIG. 1.

In particular, in dentistry, it is common for a dentist to use a syringe assembly 10 (see, for instance, FIGS. 1-3), for the purpose of injecting an anesthetic agent to patients before beginning and/or during a dental procedure. The syringe assembly 10 typically includes a handle 11 and a syringe body 12, which receives a cartridge containing the anesthetic agent, and a hollow needle 16. In operation, upon depression of the handle, the dental anesthetic agent is pushed by a plunger moving through the cartridge (not shown) through the needle 16 into the patient. At the needle end 17 of the syringe assembly 10 opposite the handle 11 is a syringe hub 14, which forms part of the syringe assembly 10, and for which the needle 16 is attached. The syringe hub 14 typically provides for a threaded attachment to the syringe assembly 10 at a syringe end 13 of the hub 14 and a threaded attachment having a screw head 15 at the needle end 17 of the hub 14. With particular reference to FIG. 2, the syringe assembly 10 includes the syringe hub 14 attached at the syringe end 13 of the hub (see FIG. 3). Also attached to a needle end 17 of the syringe assembly 10 is the needle 16 and a needle cap 20, (typically a plastic housing), for covering the needle 16 to maintain sterility of the needle 16, and also to prevent inadvertent sticks of the needle 16 into the patient and/or the healthcare personnel. As would be understood by one of ordinary skill in the art, the needle cap 20 is typically friction fit to remain in place as part of the syringe assembly 10 upon movement of the assembly, and thus prevent inadvertent exposure of the needle 16.

While there have been many attempts to provide for safe automatic removal of a needle from a syringe assembly, there are problems associated with retaining the syringe hub 14 with the syringe assembly, which has led to inadvertent disposal of this portion of the syringe assembly, leading to ensuing hazards associated with digging around in disposable sharps containers in an attempt to retrieve the syringe hub once it has been inadvertently disposed.

There also remains a need for a device and method that is capable of safely holding a syringe assembly between a first injection and completion of the dental procedure in case the healthcare personnel, e.g. the dentist, wishes to re-use the needle to supplement anesthesia dosing.

BRIEF DESCRIPTION OF THE EXEMPLARY EMBODIMENTS

An apparatus and method of automatically and safely removing a needle from a syringe assembly while retaining a syringe hub as part of the syringe assembly is generally described.

The present disclosure describes a reusable needle handling apparatus. The needle handling apparatus is configured for receiving at least a portion of a syringe assembly including at least a needle, a needle cap, and a syringe hub. The needle handling apparatus includes a first clamping mechanism having a plurality of pinch rollers. According to an aspect, the pinch rollers are configured to clamp the needle cap, and to automatically unscrew the needle from the syringe hub, so that the needle is safely and automatically removed from the syringe hub.

BRIEF DESCRIPTION OF THE DRAWINGS

A more particular description will be rendered by reference to specific embodiments thereof that are illustrated in the appended drawings. Understanding that these drawings depict only typical embodiments and are not therefore to be considered to be limiting of its scope, exemplary embodiments will be described and explained with additional specificity and detail through the use of the accompanying drawings in which.

Various features, aspects, and advantages of the embodiments will become more apparent from the following detailed description, along with the accompanying figures in which like numerals represent like components throughout the figures and text. The various described features are not necessarily drawn to scale, but are drawn to emphasize specific features relevant to some embodiments.

The headings used herein are for organizational purposes only and are not meant to limit the scope of the description or the claims. To facilitate understanding, reference numerals have been used, where possible, to designate like elements common to the figures.

DETAILED DESCRIPTION

Reference will now be made in detail to various embodiments. Each example is provided by way of explanation, and is not meant as a limitation and does not constitute a definition of all possible embodiments.

For purposes of illustrating features of the embodiments, an example will now be introduced and referenced throughout the disclosure. Those skilled in the art will recognize that this example is illustrative and not limiting and is provided purely for explanatory purposes.

Figure 4:
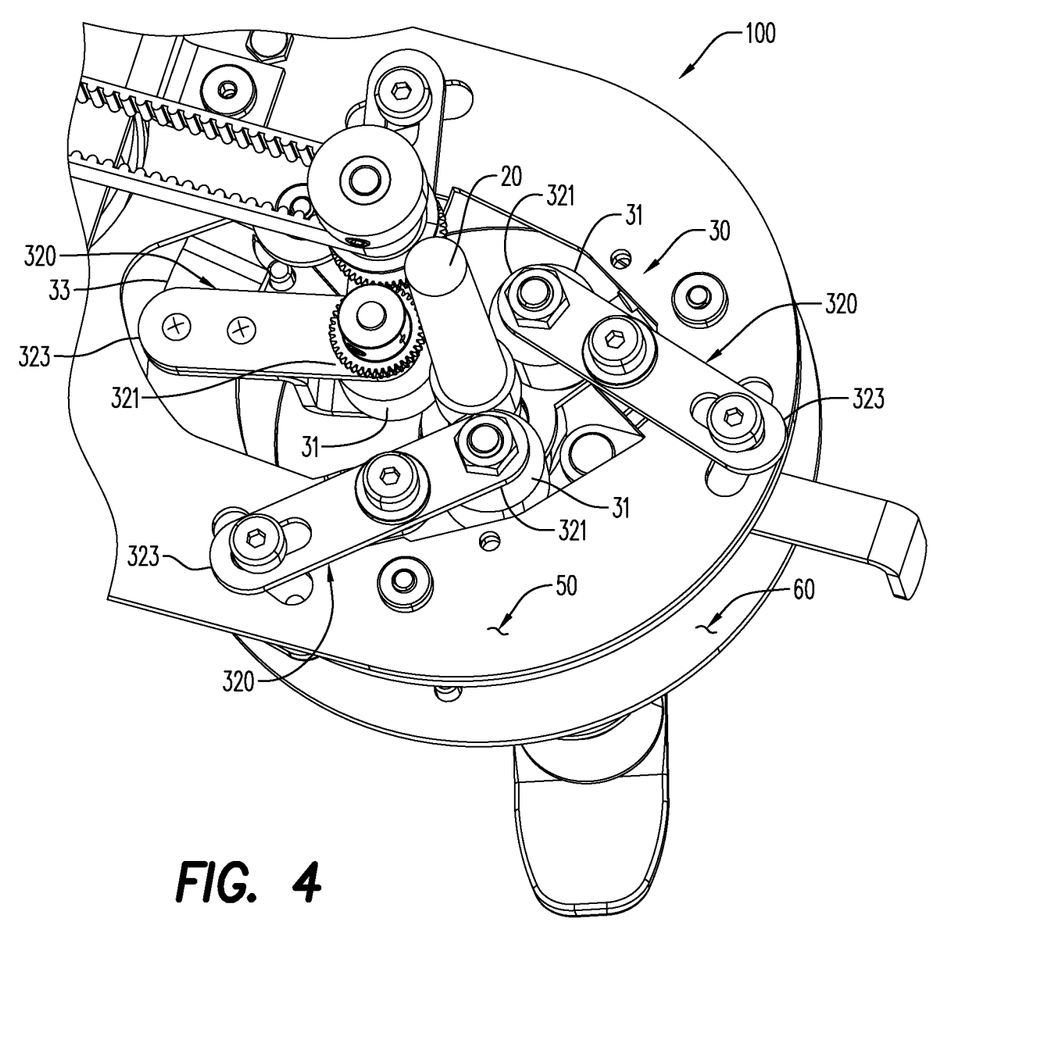
FIG. 4 is a perspective, cut-away view of the interior of a needle handling apparatus according to an embodiment, illustrating positioning of a needle cap of a syringe assembly.
Figure 5:
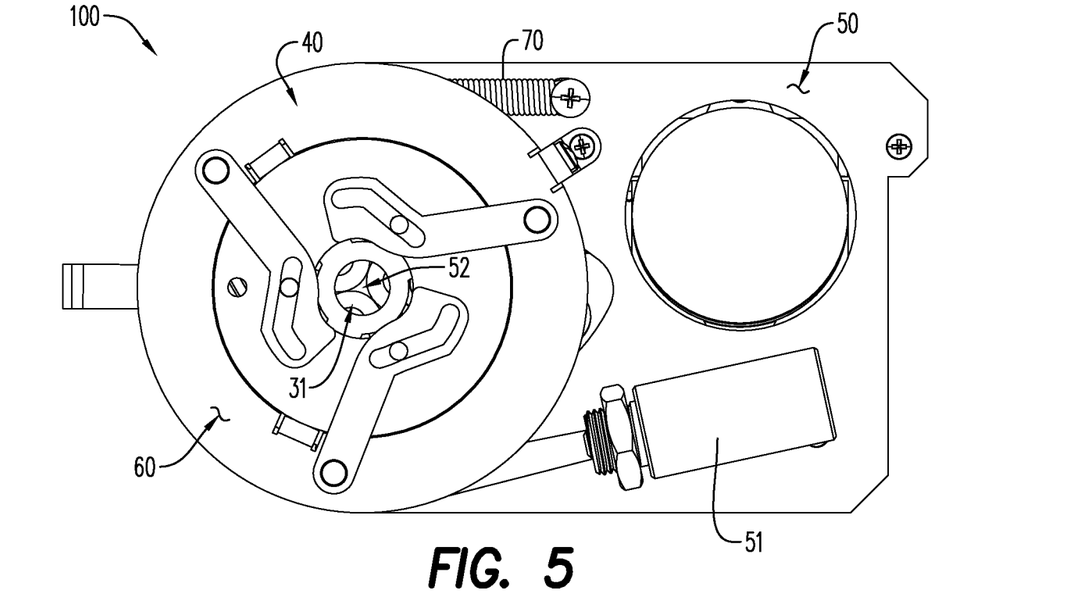
FIG. 5 is a bottom perspective view of a first clamping mechanism of a needle handling apparatus, according to an embodiment.
Figure 6:
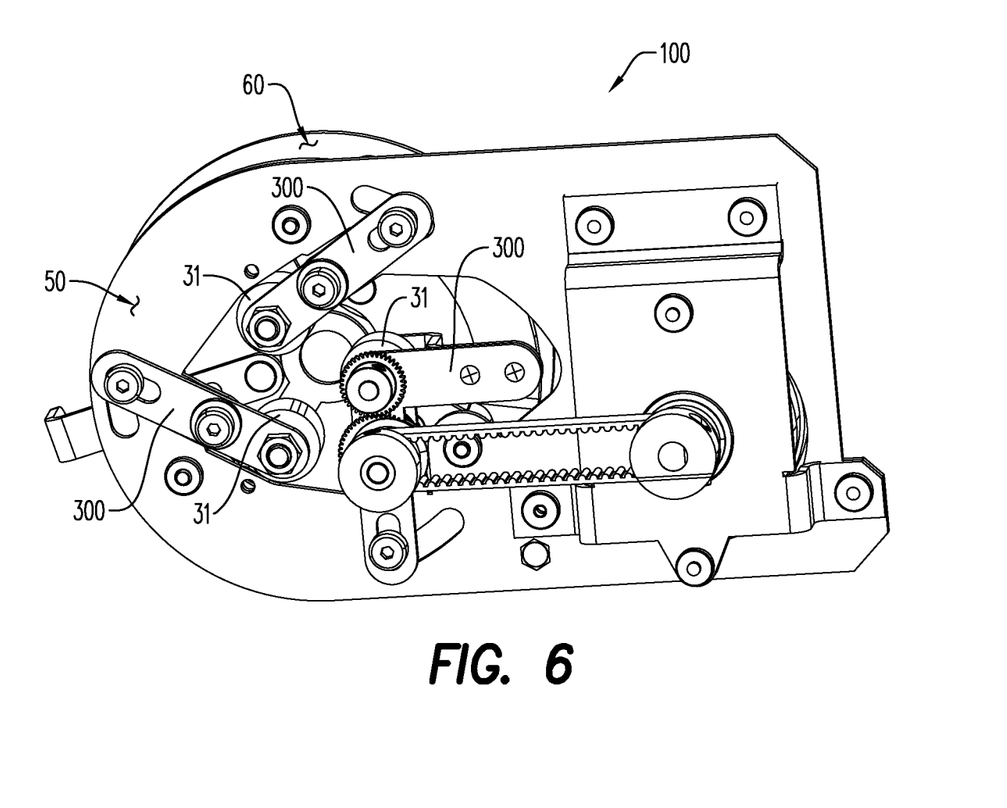
FIG. 6 is a bottom, partial perspective view of the first clamping mechanism of the needle handling apparatus of FIG. 5, illustrating positioning of a syringe assembly.

Turning now to FIGS. 4, 5, and 6, a reusable needle handling apparatus 100 is illustrated. The reusable needle handling apparatus 100 is configured for use with a syringe assembly 10 including a needle 16, a needle cap 20, and a syringe hub 14. The needle 16 may be inserted into the reusable needle handling apparatus 100 for safe removal from the syringe assembly 10.

Figure 7:
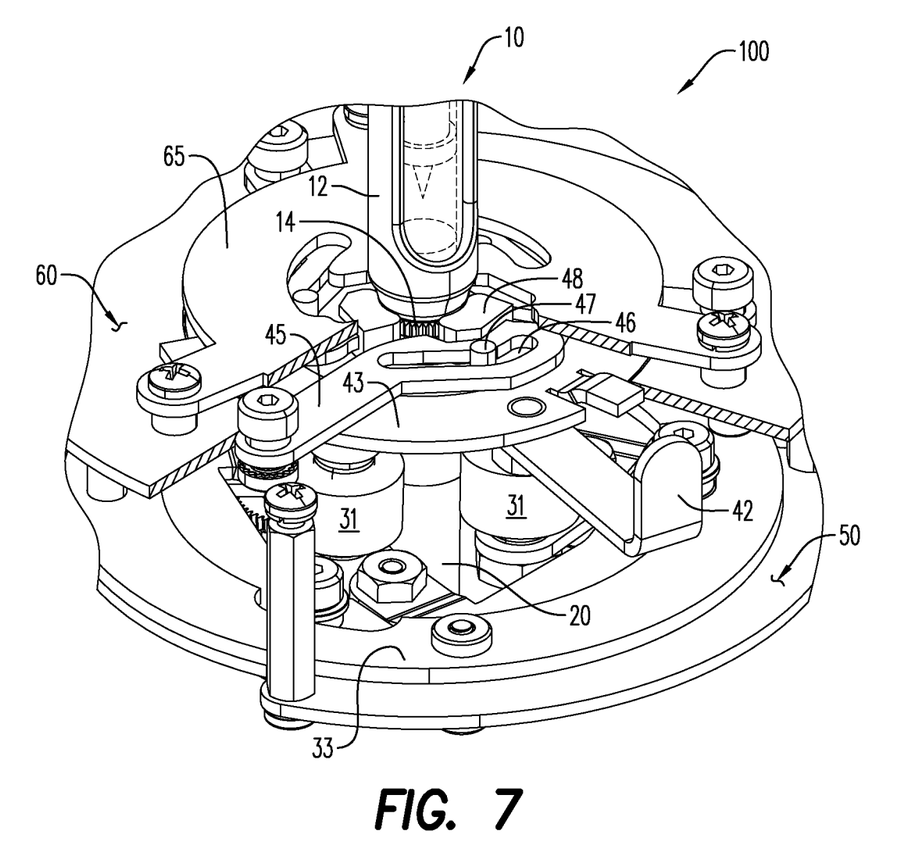
FIG. 7 is a top, perspective, and partial cut-away view of the interior of a needle handling apparatus, illustrating positioning of a syringe assembly, according to an embodiment.

The reusable needle handling apparatus 100 is illustrated as including a first clamping mechanism 30 having a plurality of pinch rollers 31. The plurality of pinch rollers 31 is configured to clamp the needle cap 20 and to unscrew the needle 16 from the syringe hub 14. According to an aspect, the pinch rollers 31 automatically unscrew the needle from the syringe hub 14. FIG. 5 shows the rollers 31 in a closed configuration, while FIG. 6 shows the rollers 31 in an open configuration. As illustrated in FIG. 7, the syringe assembly 10 may be positioned in the needle handling apparatus 100, so that the needle cap 20 is clamped between the rollers 31. The pinch rollers 31 may also clamp the syringe hub 14 in order to remove the needle 16 from the syringe assembly 10. In an embodiment, the plurality of pinch rollers 31 facilitate removal of the needle 16 and/or the needle cap 20 while retaining the syringe hub 14. In an embodiment, the plurality of pinch rollers 31 comprises rubber. Use of rubber helps the pinch rollers 31 to grip surfaces of the needle cap 20 and the syringe hub 14. In an embodiment, the plurality of pinch rollers 31 comprises at least three pinch rollers.

Figure 9:
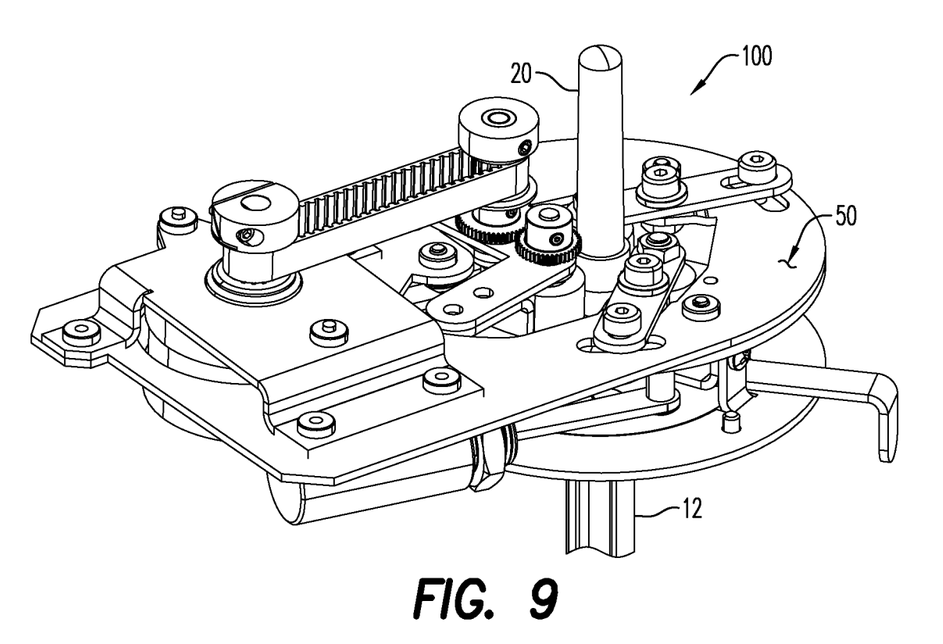
FIG. 9 is a bottom up, perspective view of FIG. 5, illustrating positioning of a syringe assembly.
Figure 10:
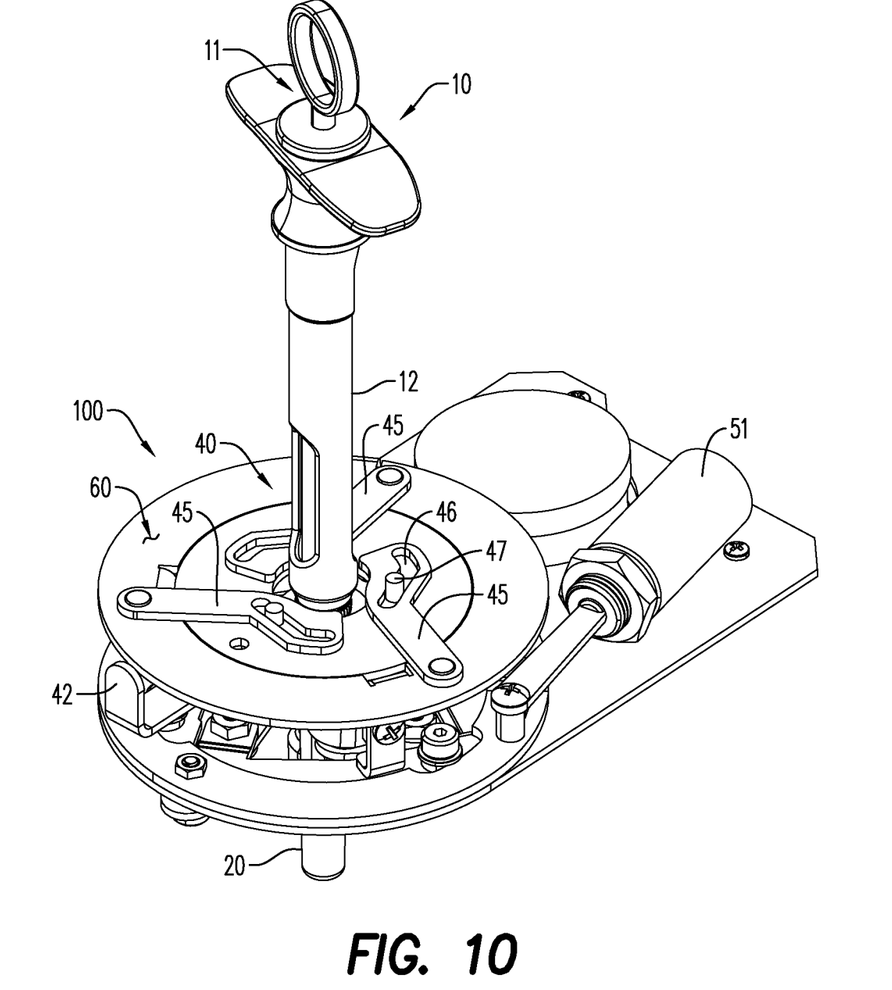
FIG. 10 is a top down, perspective view of FIG. 9.

In order to remove the needle 16 from syringe assembly 12, the plurality of pinch rollers 31 may exert a downward force on the needle cap 20. This downward force helps to ensure that the pinch rollers 31 grasp the needle cap 20 in a manner that allows the needle cap 20 to be pried free from the syringe hub 14, and be retained in the reusable needle handling apparatus 100 as illustrated in FIGS. 9-10.

In an embodiment, the plurality of pinch rollers 31 are titled at an angle (i.e., a tilt angle) in order to facilitate the removal of the needle cap 20 and, in some embodiments, the syringe hub 14. The tilt angle helps to ensure that the pinch rollers 31 grip the surface of the needle cap 20 and/or the syringe hub 14. According to an aspect, when the first clamping mechanism 30 is actuated, the plurality of pinch rollers 31 may rotate. During the rotation, the tilt angle of the pinch rollers 31 may help to exert the downward force on the needle cap 20. According to an aspect, as the rollers 31 advance down a distance D1 on the threads 15 of the syringe hub 14, the downward force being exerted may push the needle 16 downwardly at a similar distance D2. This helps to remove the needle 16 and/or the needle cap 20 from the syringe hub 14. In an embodiment, the tilt angle of the plurality of pinch rollers 31 may be up to about 5.0°, alternatively from about 1.5° to about 5.0°, alternatively from about 3.5° to about 5.0°, alternatively from about 3.7° to about 4.7°. In an embodiment, the screw thread 15, which is located at the needle end 17 of the syringe assembly 10, comprises a helix angle. The helix angle may be about 1.0° to about 2.0°, alternatively about 1.5° to about 2.0°. According to an aspect, the helix angle is about 1.47°. The tilt angle of the plurality of pinch rollers 31 is the same angle as the helix angle of the screw thread 15. As would be understood by one of ordinary skill in the art, the tilt angle of the plurality of pinch rollers 31 may be designed to that they correspond with or are substantially identical to the helix angle of screw threads of any syringe assembly.

Figure 8:
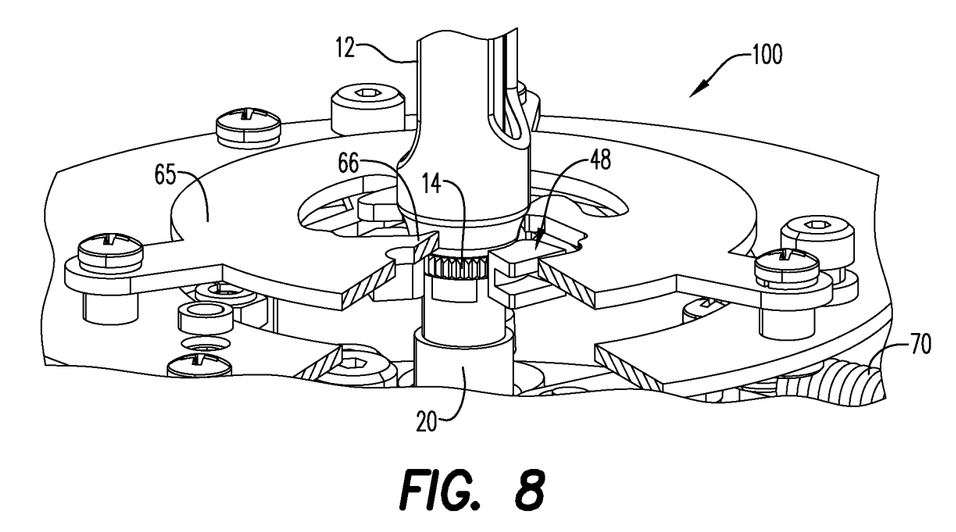
FIG. 8 is a top, perspective and partial cut-away view of the needle handling apparatus, illustrating a limit plate, according to an embodiment.

In the illustrative example and as seen in FIGS. 5, 6-7, the needle end 17 of the syringe assembly 10 is inserted into a void/opening 52 (FIG. 5) of the needle handling apparatus 100. In an embodiment, the void 52 is configured to receive a portion of the syringe hub 14 (FIG. 8). Once the syringe hub 14 is received therein, the syringe hub 14 may be maintained in that position.

The first clamping mechanism 30 of needle handling apparatus 100 is configured to hold the syringe assembly 10 to facilitate removal of the needle 16 and/or the needle cap 20 while retaining the syringe hub 14. In other words, the syringe hub 14 remains attached to the syringe assembly 10, while the syringe body 12 may be removed therefrom.

In an embodiment, the first clamping mechanism 30 includes a cam mechanism 300. The plurality of pinch rollers 31 may be rotatably coupled to the cam mechanism 300, as seen for instance, in FIGS. 5-6. Actuation of the cam mechanism 300 causes the plurality of pinch rollers 31 to engage with or come into contact with the syringe hub 14. The actuation of the cam mechanism 300 may be facilitated by a tension spring 70. The spring 70 may be positioned on a release plate 33 and may be connected to a plurality of spring adjusters (not shown). The spring adjusters may be configured as arms that connect to the release plate 33 by sock head screws 49 (operably similar to the slot arrangement described hereinbelow with reference to FIG. 7). Movement of the screw 49 through a slot of the spring adjusters may be operable for expanding and/or contracting the spring 70. According to an aspect, this movement is facilitated by activation of the motor assembly 51. As would be understood by one of ordinary skill in the art, various other actuation methods may be employed. The cam mechanism 300 is illustrated as having a plurality of arms 320. The arms 320 may extend between the pinch rollers 31 and the release plate 33 of the first clamping mechanism 30. In an embodiment, each of the plurality of arms 320 is coupled at a first end 321 to one of the plurality of pinch rollers 31 and coupled at a second end 323 to the release plate 33. The arms 320 may be coupled to the pinch rollers 31 and/or the release plate 33 by a screw and nut system.

According to an aspect, the first clamping mechanism 30 includes a motor assembly 51. When the first clamping mechanism 30 is actuated as described hereinabove, for example, the motor assembly 51 drives rotation of at least one of the plurality of pinch rollers 31. This facilitates the removal of the needle 16 and/or the needle cap 20. In an embodiment, the first clamping mechanism 30 is assembled with the motor assembly 51 using a mounting bracket 50.

In the illustrative example as seen in FIGS. 4-7, the needle handling apparatus 100 further includes an upper chassis 60. The upper chassis 60 is fixedly mounted to the mounting bracket 50.

In an embodiment, the reusable needle handling apparatus 100 includes a second clamping mechanism 40 configured to clamp the syringe hub 14. As illustrated in FIG. 7, the second clamping mechanism 40 includes a syringe clamping plate 43 that is rotatably coupled to the upper chassis 60. The syringe clamping plate 43 may is illustrated as abutting a plurality of jaws/clamps 45. The jaws 45 may be sandwiched between the clamping plate 43 and a limit plate 65 (described in further detail hereinbelow). According to an aspect, the jaws 45 are configured to clamp the syringe hub 14. While the reusable needle handling apparatus 100 is illustrated as having three jaws 45, it is to be understood that more or less jaws 45 may be sufficient to perform the stated function. As such, the syringe clamping plate 43 may include 2, 3, 4, 5, 6, or more jaws 45. According to an aspect, during rotation, the second clamping mechanism 40 is pushed away from the mounting bracket 50, while the arms 320 grasp the needle cap 20, via the cam mechanism 300.

As shown in the illustrative example as seen in FIG. 7, each of the plurality of jaws 45 includes a slot 46 that slidably engages a pin 47. The pin 47 is able to move within the slot 46, to facilitate at least a partial rotation of the one or more components of the reusable needle handling apparatus 100.

According to an aspect and as illustrated in FIGS. 7-8, the reusable needle handling apparatus 100 includes a shoe 48. The shoe 48 may be disposed around a portion of the slot 52. Each of the plurality of jaws 45 engages with the shoe 48, in such a manner that the shoe 48 contacts the syringe hub 14. The shoe 48 may be composed of any material that is able to grip the surface of the syringe assembly 10, such as the syringe hub 14. According to an aspect, the shoe 48 includes rubber to facilitate frictional engagement between the shoe 48 and the surface of the syringe assembly 10.

In an embodiment, the syringe clamping plate 43 includes a lever 42 configured to rotate the syringe clamping plate 43. In an embodiment, actuation of the lever 42 may also actuate the motor assembly 51 to initiate rotation of at least one of the plurality of pinch rollers 31. While certain embodiments include manual functions, such as lever 42, to rotate the syringe clamping plate 43 and/or initiate actuation of motor assembly 51, these functions may be automated via sensors, electro-mechanical components, control electronics, firmware, and the like.

In an embodiment and as illustrated in FIGS. 7-8, the needle handling apparatus 100 further comprises a limit plate 65. The limit plate 65 is configured to prevent over-insertion of the syringe assembly 10 into the needle handling apparatus 100. In an embodiment, the limit plate 65 comprises at least one lip 66 configured to contact the syringe body 12. The lip 66 may be a protrusion that extends from the surface of the limit plate 65.

The present disclosure, in various embodiments, configurations and aspects, includes components, methods, processes, systems and/or apparatus substantially developed as depicted and described herein, including various embodiments, sub-combinations, and subsets thereof. Those of skill in the art will understand how to make and use the present disclosure after understanding the present disclosure. The present disclosure, in various embodiments, configurations and aspects, includes providing devices and processes in the absence of items not depicted and/or described herein or in various embodiments, configurations, or aspects hereof, including in the absence of such items as may have been used in previous devices or processes, e.g., for improving performance, achieving ease and/or reducing cost of implementation.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

In this specification and the claims that follow, reference will be made to a number of terms that have the following meanings. The terms "a" (or "an") and "the" refer to one or more of that entity, thereby including plural referents unless the context clearly dictates otherwise. As such, the terms "a" (or "an"), "one or more" and "at least one" can be used interchangeably herein. Furthermore, references to "one embodiment", "some embodiments", "an embodiment" and the like are not intended to be interpreted as excluding the existence of additional embodiments that also incorporate the recited features. Approximating language, as used herein throughout the specification and claims, may be applied to modify any quantitative representation that could permissibly vary without resulting in a change in the basic function to which it is related. Accordingly, a value modified by a term such as "about" is not to be limited to the precise value specified. In some instances, the approximating language may correspond to the precision of an instrument for measuring the value. Terms such as "first," "second," "upper," "lower" etc. are used to identify one element from another, and unless otherwise specified are not meant to refer to a particular order or number of elements.

As used herein, the terms "may" and "may be" indicate a possibility of an occurrence within a set of circumstances; a possession of a specified property, characteristic or function; and/or qualify another verb by expressing one or more of an ability, capability, or possibility associated with the qualified verb. Accordingly, usage of "may" and "may be" indicates that a modified term is apparently appropriate, capable, or suitable for an indicated capacity, function, or usage, while taking into account that in some circumstances the modified term may sometimes not be appropriate, capable, or suitable. For example, in some circumstances an event or capacity can be expected, while in other circumstances the event or capacity cannot occur—this distinction is captured by the terms "may" and "may be."

As used in the claims, the word "comprises" and its grammatical variants logically also subtend and include phrases of varying and differing extent such as for example, but not limited thereto, "consisting essentially of" and "consisting of." Where necessary, ranges have been supplied, and those ranges are inclusive of all sub-ranges therebetween. It is to be expected that variations in these ranges will suggest themselves to a practitioner having ordinary skill in the art and, where not already dedicated to the public, the appended claims should cover those variations.

The terms "determine", "calculate" and "compute," and variations thereof, as used herein, are used interchangeably and include any type of methodology, process, mathematical operation or technique.

The foregoing discussion of the present disclosure has been presented for purposes of illustration and description. The foregoing is not intended to limit the present disclosure to the form or forms disclosed herein. In the foregoing Detailed Description for example, various features of the present disclosure are grouped together in one or more embodiments, configurations, or aspects for the purpose of streamlining the disclosure. The features of the embodiments, configurations, or aspects of the present disclosure may be combined in alternate embodiments, configurations, or aspects other than those discussed above. This method of disclosure is not to be interpreted as reflecting an intention that the present disclosure requires more features than are expressly recited in each claim. Rather, as the following claims reflect, the claimed features lie in less than all features of a single foregoing disclosed embodiment, configuration, or aspect. Thus, the following claims are hereby incorporated into this Detailed Description, with each claim standing on its own as a separate embodiment of the present disclosure.

Advances in science and technology may make equivalents and substitutions possible that are not now contemplated by reason of the imprecision of language; these variations should be covered by the appended claims. This written description uses examples to disclose the method, machine and computer-readable medium, including the best mode, and also to enable any person of ordinary skill in the art to practice these, including making and using any devices or systems and performing any incorporated methods. The patentable scope thereof is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal language of the claims.

What is claimed is:

1. A reusable needle handling apparatus comprising:
   at least a portion of a syringe assembly including at least a needle, a needle cap, and a syringe hub;
   a first clamping mechanism comprising a plurality of pinch rollers configured to clamp the needle cap and to automatically unscrew the needle from the syringe hub;
   a motor assembly configured to drive rotation of at least one pinch roller of the plurality of pinch rollers;
   a second clamping mechanism configured to clamp the syringe hub, wherein the second clamping mechanism comprises:
      a syringe clamping plate, and
      a plurality of jaws abutting the syringe clamping plate;
   wherein the syringe clamping plate is rotatably coupled to an upper chassis, and the syringe clamping plate comprises a lever configured to rotate the syringe clamping plate.

2. The needle handling apparatus of claim 1, wherein the plurality of pinch rollers are configured to exert a downward force on the needle cap.

3. The needle handling apparatus of claim 1, wherein the first clamping mechanism further comprises a release plate.

4. The needle handling apparatus of claim 1, wherein the first clamping mechanism is assembled with the motor assembly using a mounting bracket.

5. The needle handling apparatus of claim 4, wherein the upper chassis is fixedly mounted to the mounting bracket.

6. The needle handling apparatus of claim 1, wherein the motor assembly is actuated by actuation of the lever to cause the syringe clamping plate to clamp the syringe hub, and wherein the actuation of the motor assembly rotates the at least one pinch roller of the plurality of pinch rollers.

7. A reusable needle handling apparatus comprising:
   at least a portion of a syringe assembly including at least a needle, a needle cap, and a syringe hub;
   a first clamping mechanism comprising:
      a plurality of pinch rollers configured to clamp the needle cap and to automatically unscrew the needle from the syringe hub, and
      a cam mechanism configured to draw the pinch rollers into contact with the needle cap; and
   a second clamping mechanism configured to clamp the syringe hub, wherein the second clamping mechanism comprises:
      a syringe clamping plate, and
      a plurality of jaws abutting the syringe clamping plate;
   wherein the syringe clamping plate is rotatably coupled to an upper chassis and comprises a lever configured to rotate the syringe clamping plate.

8. The needle handling apparatus of claim 7, wherein the first clamping mechanism further comprises a release plate.

9. The needle handling apparatus of claim 8, further comprising:
   a tension spring coupled to the release plate,
   wherein the tension spring is configured to actuate the cam mechanism.

10. The needle handling apparatus of claim 7, further comprising:
    a limit plate configured to prevent over-insertion of the syringe assembly into the needle handling apparatus.

* * * * *